United States Patent [19]

Oetjen et al.

[11] 4,318,398

[45] Mar. 9, 1982

[54] HUMIDITY EXCHANGER FOR A BREATHING APPARATUS

[75] Inventors: Georg-Wilhelm Oetjen, Lübeck; Frank Benthin, Lübeck-Hamberge, both of Fed. Rep. of Germany

[73] Assignee: Drägerwerk Aktiengesellschaft, Fed. Rep. of Germany

[21] Appl. No.: 159,393

[22] Filed: Jun. 13, 1980

[30] Foreign Application Priority Data

Jul. 21, 1979 [DE] Fed. Rep. of Germany ....... 2929584

[51] Int. Cl.³ .............................................. A61M 16/00
[52] U.S. Cl. ........................ 128/201.13; 128/204.13; 128/204.17; 165/141; 165/DIG. 10; 261/DIG. 65
[58] Field of Search ................... 128/201.13, 204.13, 128/204.15, 204.17, 203.26, 203.27; 165/140, 141, 133, DIG. 10; 261/DIG. 65, 104

[56] References Cited

U.S. PATENT DOCUMENTS

| | | | |
|---|---|---|---|
| 1,123,201 | 12/1914 | Almirall | 165/140 |
| 2,670,933 | 3/1954 | Bay | 165/140 |
| 3,565,072 | 2/1971 | Gauthier | 128/204.15 |
| 3,871,373 | 3/1975 | Jackson | 128/203.27 |
| 4,010,748 | 3/1977 | Dobritz | 128/203.27 |
| 4,146,597 | 3/1979 | Eckstein et al. | 128/204.13 |
| 4,150,671 | 4/1979 | Tiger | 128/201.13 |
| 4,155,961 | 5/1979 | Benthin | 128/204.13 |

*Primary Examiner*—Henry J. Recla
*Attorney, Agent, or Firm*—McGlew and Tuttle

[57] ABSTRACT

A humidity exchanger for a breathing apparatus includes an outer housing having one end with an opening for the passage of inspiration and expiration air therethrough and an opposite end into which is fitted a separate inner housing. The inner housing carries a first tube bundle of fibrous tubules defining passages therethrough for the passage of either inspiration or expiration air. This passage contains spaced apart packings through which the tubules extend and spaced between the packings defines a heat exchange space around the tubules. Construction includes an inner tube or conduit centrally of the bundle with a passage of heat of the inspiration or the expiration air into the space surrounding the tubules within the inner housing. The inner housing leads into a front space of the outer housing through a conduit connected to the user of the apparatus. The space between the inner housing and the outer housing is filled with a second tubule bundle which is embedded at each end in packing so that an entrance passage is defined adjacent the rear end of the outer housing which connects with the space defined around the first bundle of tubules in the inner housing. Here again the space around the second bundle between the inner and outer housings is connected with an inlet and an outlet for circulating a conditioning fluid, for example, such as warm water for heating inspiration air in the event the inspiration air is passed through the second bundle tubules. The front end of the tubules of the second bundle communicate with an inflow space which is closed by a non-return valve which permits flow in a direction toward the conduit front end which is to be connected to the user.

4 Claims, 1 Drawing Figure

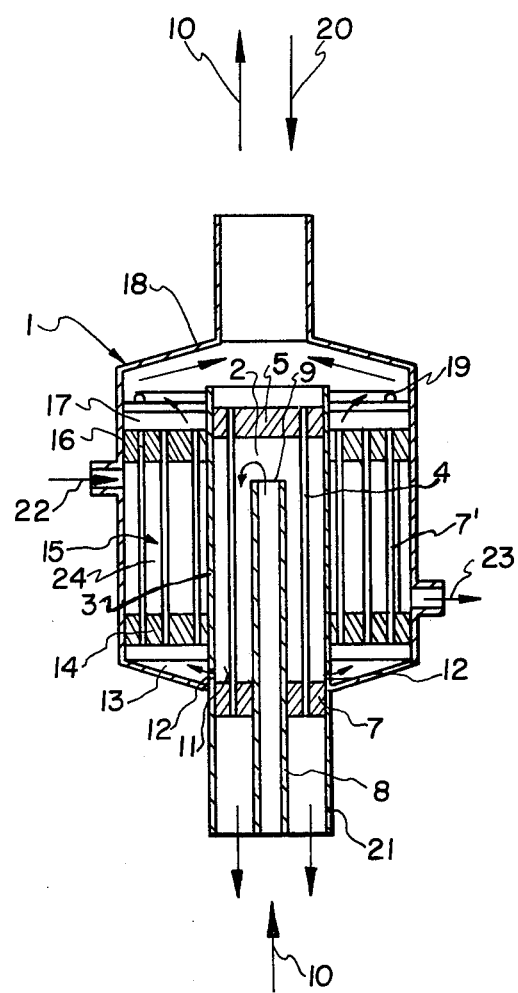

HUMIDITY EXCHANGER FOR A BREATHING APPARATUS

FIELD AND BACKGROUND OF THE INVENTION

This invention relates in general to a construction of respirator devices and in particular to a new and useful humidity exchanger for a breathing device.

In breathing devices it must be ensured that the air passages of the patients do not dry out and that his heat balance is not disturbed. The risk exists particularly when the cold inhaled air is supplied to the patient through a tracheotomy tubule or through an intratracheal catheter. In these cases the rhinopharingeal area, where the inhaled air is normally humidified and heated, is bypassed.

In order to prevent drying and cooling, it is known to provide ventilating air humidifiers to bring the inhaled air to a volume of more than 70% relative humidity, and approximately to body temperature.

Subdivided according to the principal design, ventilating air humidifiers are known with humidification of the ventilating air from a water supply and by a humidity exchange from the humid exhaled air into the relatively dry inhaled air.

In a ventilating air humidifier from a water supply, the supply of the ventilating air is effected from an air supply to the patient through a corrugated hose, inside this hose is arranged a folded water-carrying hose which is connected with its connection to the water supply. The wall of the water hose is waterproof, but is permeable to water vapor. The ventilating air conducted through the corrugated hose surrounds the water-carrying hose. It is humidified by the water passing through in vapor form. In a further development, the ventilating gas-carrying hose can be arranged in a water bag hanging around the neck of the user connected into the ventilating gas connection to the breathing apparatus or directly from the surrounding atmosphere to the user. The breathing hose with polytetrafluorethylene walls, extending in ascending and descending turns, can be a part of the water bag. Its inlet can be connected either directly to the atmosphere or to a portable container with liquid oxygen. Its outlet leads to a tracheotomy tubule or to a nose catheter. It is indicated that the water supply is heated by the body heat.

A disadvantage is the relatively large water supply which is necessary and whose temperature must be controlled and whose large volume close to the patient is always a potential risk when the water supply runs out. Adequate humidification of the ventilating air of the ventilating gas requires larger diameters for the ventilating air guide. These known ventilating air humidifiers are therefore very large. Heating the inhaled air by the body temperature over the water supply is also very problematic (U.S. Pat. No. 3,871,373).

Another known ventilating air humidifier for respiration with humidification from a water supply also contains a waterproof foil which is permeable, however, to water vapor and which is charged on one side with warm water, while the ventilating gas to be humidified passes by the other side charged with gas.

The evaporation surface is made in star form to achieve a greater evaporative power. In order to further reduce the size of the ventilating air humidifier without reducing the evaporation surface and thus the evaporative power, the water vapor-permeable foil was formed in an additional patent by the walls of hollow fibers. The hollow fibers are arranged as a bundle parallel to each other in a housing. They are secured together with a water feed and a water discharge pipe on the end faces of a packing. The water to be evaporated is fed and discharged through the water carrying pipes. It wets the hollow fibers.

This type of ventilating air humidifier also depends directly on a relatively large water supply. The heating requires special measures (German Pat. No. 24 30 875 with additional U.S. Pat. No. 2,617,985).

In a known humidity exchanger in apparatus for ventilation and anesthesia, in which the humidity contained in the ventilating air is separated, and the separated water is evaporated into the inhaled air, the respiration and expiration channels extending in counter-flow have a diffusion foil as a common partition so that the water contained in the exhaled air in vapor form can get by diffusion through the diffusion foil into the inhaled air. In order to prevent the heat contained in the exhaled air from escaping into the surrounding atmosphere, the humidity exchanger can be surrounded by a heat insulation. Humidity exchangers of this type are very large. An adequate passage of water vapor requires a corresponding large foil surface in long expiration and inspiration air channels. The heat insulation must insulate these channels well from the atmosphere so that the inhaled air is sufficiently heated. (DOS No. 25 29 050).

SUMMARY OF THE INVENTION

The present invention provides a humidity exchanger that can be used for long periods of time.

In accordance with the invention a humidity exchanger for a breathing apparatus is constructed such that the exhaled and inhaled air passages or guides have a common partition and the humidity contained in the exhaled air and the heat content are transported through the partition into the inhaled air. Construction includes a rehumidifier portion supplied with a tepid fluid such as water in addition to an inner exchange unit which is used for the transport of humidity and temperature between the inhaled and exhaled air.

Accordingly, it is an object of the invention to provide an improved humidity exchanger which includes a tubule arrangement for the passage of one of either inhaled or exhaled air and a base around the tubules for the passage of the other. In addition, the construction includes an inner and outer housing which contain separate tubular bundles for the passage of one of the two exchange media, inspiration air or expiration air. The flow of a medium such as inspiration air will be into its base around the first bundle and then into or through the tubules of the second bundle. The expiration air will be through only the tubules of the first bundle and the second tubular bundle will conditioned by a control fluid which is circulated in the space around the second tubule bundle.

The advantage achieved result from the rehumidification of the inhaled air which is already prehumidified and heated with the humidity and heat energy of the exhaled air. The warm water of the rehumidifier ensures both the heat balance for the user, and a high relative humidity in the inhaled air. A small amount of water and heat energy are already sufficient. The rehumidifier increases only slightly the total dimensions of the exchanger. It remains simple in design and easy to handle.

Due to the prehumidification, the humidity is removed from the exhaled air to such an extent that a water trap is no longer necessary when the humidity exchanger is installed in a patient system.

A further object of the invention is to provide a humidity exchanger in a breathing device which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawing and descriptive matter in which a preferred embodiment of the invention is illustrated.

BRIEF DESCRIPTION OF THE DRAWING

In the Drawing:

The only FIGURE of the drawing is an axial sectional view of a humidity exchanger constructed in accordance with the invention.

DESCRIPTION OF THE PREFERRED EMBODIMENT

Referring to the drawing in particular the invention embodied therein comprises a humidity exchanger for a breathing apparatus which includes an outer housing generally designated 1 having a bore extending therethrough with a front end connecting piece 18 defining a conduit with an outlet opening which provides means for conducting inhalation air in the direction of the arrow 10 or exhalation air in the direction of the arrow 20 during separate times of a breathing cycle. In the construction of the invention, an inner tubular housing 3 is mounted concentrically with the housing 1 and extends through the rear end inlet opening 6 of the housing 1 and is spaced from the opposite end and the interior thereof. This inner housing 3 has a passage which contains a first bundle 4 of fiber tubules which are embedded at the respective ends in axially spaced first packings 5 and 7. The tubules comprise hollow fiber tubes which permit exchange of water vapor and heat with a medium surrounding the outside thereof. A space 11 is defined around the exterior of the tubules and one of the media, for example, inhalation air is directed in a direction of arrow 10 through the inlet opening defined in an inner connecting socket or conduit 21 via an inhalation air guide 8 into the space 11 through an opening 12 into a rear closed space 13 defined between the inner and outer housings.

The humidity exchanger contains on the outer common housing 1, an exchange body 2 composed of the inner housing 3, with the passage axially extending therethrough from a first open end to a second open end, with the first bundle 4 of hollow fiber tubes or tubules, extending parallel to each other in the passage and held in the first packings 5 and 7. In the first bundle of tubes 4, an inhalation air guide 8 is located within the inner tubular housing in spaced concentric relationship therewith in communication with the first open endin the inner tubular housing defined by connecting socket 21. The inhaled air passes from the guide 8 through the second open end 9, flows through a space 11 around hollow fiber tubes 4 and leaves inner housing 3 again through wall openings 12, to flow into in-flow space 13 below one packing 14 of two second axially spaced packing 14,16 of a second bundle 15. A second bundle 15 with waterwetted hollow tubes 7' is held at the top by packing 16. Warm water is fed through a water feed 22 to space 24 around hollow fiber tubes 7' of the second bundle 15 and discharged from the latter through a water discharge 23. An in-flow space 17 above packing 16 is terminated by non-return valve 19 opening away from the latter into the interior of connecting piece or socket 18.

The humidity exchanger works as follows:

The inhaled air 10 flows through inhaled air guide 8 into the space 11 around the first bundle 4 of hollow fiber tubes. There it surrounds the hollow fiber tubes in the space 11 and flows through openings 12 into in-flow space 13 in front of packing 14. From there the interiors of the hollow fiber tubes 7' of the second bundle 15 are traversed up to flow of space 17 behind packing 16. The inhaled air 10 then flows through the opening non-return valve 19 and the interior of connecting socket 18 to the user.

The exhaled air 20 flows over connecting socket 18 through the hollow fiber tubes of the first bundle 4, through connecting socket 21 out of the humidity exchanger.

The following humidity and heat conditions prevail during the flow:

(a) The dry and cold inhaled air 10 absorbs in the first bundle 4 the humidity and heat energy taken from the previously traversed exhaled air 20.

(b) In the second bundle 15 the inhaled air 10 is further humidified and heated.

(c) Warm and humid inhaled air is fed to the user.

(d) The exhaled air 20 leaves behind the humidity and heat energy in the first bundle 4.

A suitable hollow fiber tubule comprises a thin permeation diaphragm which is carried by a supporting construction. The thickness of the diaphragm is of the order of a few microns, it depends on the requirements of the permeation; the thickness of the supporting construction depends on the mechanical load.

While a specific embodiment of the invention has been shown and described in detail to illustrate the application of the principles of the invention, it will be understood that the invention may be embodied otherwise without departing from such principles.

What is claimed is:

1. A humidity exchanger for a breathing apparatus comprising an outer tubular housing having a passage extending therethrough for passing inspiration and expiration air from an first opening to an opposite opening, an inner tubular housing extending into said passage and mounted to said second opening, said inner tubular housing having a passage axially extending therethrough from said first open end exterior to said outer housing to a second open end in said outer housing spaced from said first opening, axially spaced first packings disposed in said passage of said inner tubular housing, an insulation air guide tube located within said inner tubular housing in spaced concentric relation therewith adjacent said first open end and extending through one of said first packings into and communication with said passage within said inner tubular housing between said first packings, a first bundle of vapor permeable fiber tubes in said inner housing passage having opposite open end portions extending through said first packings in communication with said first and second openings in said outer housing, axially spaced second packings disposed around said inner housing between said inner housing and said outer housing defining a fluid exchange chamber bound by said second packings, said inner tubular housing and said outer tubular housing, a second bundle of vapor permeable fiber tubes in said chamber having respective opposite open ends extending through said second packings, an inflow space defined between a first one of said second packings, said outer tubular housing adjacent said second opening, and said tubular housing, means for circulating a fluid through said fluid exchange chamber, said inflow space being in fluid communication with a first one of said opposite open ends of said second bundle of fiber tubes, said inner tubular housing having a wall portion adjacent said inflow space with wall openings extending therethrough for establishing fluid communication between said passage of said inner housing and said inflow space, a non-return valve means mounted to said inner tubular housing and said outer tubular housing between said first opening and a second one of said second packings and operable to pass a flow of inspiration air from said second bundle of fiber tubes to said first opening and to prevent a flow of expiration air from passing into said second bundle of fibers tubes from said first opening, whereby a flow of the inspiration air may be directed into said second opening of said outer housing and through said inhalation air guide tube, then into said passage of said inner housing, through said wall openings into said inflow space, then through said fiber tubes of said second bundle, through said return valve means and through said first opening, and whereby a flow of expiration air may be directed through said first opening into said tubes of said first bundle and out through said second opening.

2. A humidity exchanger according to claim 1, wherein said circulating means includes means for circulating warm water through said chamber between said outer housing and said inner housing and around said tubes of said second bundle.

3. A humidity exchanger according to claim 1, wherein said circulating means comprises a water inlet and a water discharge.

4. A humidity exchanger according to claim 1, wherein said fiber tubes permit exchange of water vapor and heat with a medium surrounding the outside thereof.

* * * * *